United States Patent
Pointillart et al.

(10) Patent No.: US 7,335,232 B2
(45) Date of Patent: Feb. 26, 2008

(54) METHOD FOR REPAIRING BONE

(75) Inventors: Vincent Pointillart, Bordeaux (FR);
Guy Deneuvillers, Merlimont (FR);
Sebastien Meliot, Bertreville Saint Ouen (FR)

(73) Assignee: Cousin Biotech, Wervicq Sud (FR)

( * ) Notice: Subject to any disclaimer, the term of this patent is extended or adjusted under 35 U.S.C. 154(b) by 0 days.

(21) Appl. No.: 11/580,977

(22) Filed: Oct. 16, 2006

(65) Prior Publication Data

US 2007/0073401 A1    Mar. 29, 2007

Related U.S. Application Data

(63) Continuation of application No. 10/466,931, filed as application No. PCT/FR02/00311 on Jan. 25, 2002, now Pat. No. 7,208,015.

(30) Foreign Application Priority Data

Jan. 25, 2001   (FR)   ................... 01 01011

(51) Int. Cl.
*A61F 2/30* (2006.01)
*A61F 2/44* (2006.01)

(52) U.S. Cl. .............. 623/23.51; 623/23.75; 606/69

(58) Field of Classification Search .......... 623/16.11, 623/23.28, 23.3, 23.36, 23.46, 23.51, 23.52, 623/23.54, 23.55, 23.57, 23.59, 23.6, 23.61, 623/23.63, 23.75, 23.76; 606/61, 69, 70, 606/72, 76, 77, 86, 151, 154
See application file for complete search history.

(56) References Cited

U.S. PATENT DOCUMENTS

| | | |
|---|---|---|
| 4,820,305 A | 4/1989 | Harms et al. |
| 5,030,233 A | 7/1991 | Ducheyne |
| 5,139,424 A | 8/1992 | Yli-Urpo |
| 5,211,664 A | 5/1993 | Tepic et al. |
| 5,329,846 A | 7/1994 | Bonutti |
| 5,397,359 A | 3/1995 | Mittelmeier et al. |
| 5,480,442 A | 1/1996 | Bertagnoli |
| D403,069 S | 12/1998 | Drewry et al. |
| 6,214,049 B1 | 4/2001 | Gayer et al. |
| 6,319,255 B1 | 11/2001 | Grundei et al. |

FOREIGN PATENT DOCUMENTS

| | | |
|---|---|---|
| DE | 91 15 341 | 2/1992 |
| EP | 268 115 | 5/1988 |
| EP | 475 077 | 3/1992 |
| EP | 630 625 | 12/1994 |
| EP | 968 692 | 1/2000 |
| WO | WO 88/10100 | 12/1988 |
| WO | WO 98/26725 | 6/1998 |
| WO | WO 99/51171 | 10/1999 |
| WO | WO 01/03614 | 1/2001 |

*Primary Examiner*—Eduardo C. Robert
*Assistant Examiner*—Davic Comstock
(74) *Attorney, Agent, or Firm*—Leydig, Voit & Mayer, Ltd.

(57) ABSTRACT

A method for repairing bone in a bone cavity delimited by healthy bone faces, and from which traumatized bone has been excised, comprises adjusting a flexible, biocompatible mesh fabric tube to fit the bone cavity and contact the healthy bone faces and filling the mesh tube with a bone graft. A bioresorbable coating is applied to the tube to rigidify the tube having been adjusted in shape to fit the bone cavity. The coating seals the mesh against graft movement through the mesh of the tube until the bioresorbable coating has been resorbed. The tube is inserted within the bone cavity and the coating is resorbed to allow the graft to pass from the interior of the tube, through the mesh, to the healthy bone faces.

8 Claims, 1 Drawing Sheet

METHOD FOR REPAIRING BONE

This application is a continuation of application Ser. No. 10/466,931, filed Nov. 20, 2003, now U.S. Pat. No. 7,208,015, which is a 371 of PCT/FR02/00311, filed Jan. 25, 2002.

FIELD OF INVENTION

The subject of the present invention is a device for bone repair by arthrodesis, intended to be used for the reconstitution of bone trauma, cervical vertebrae in particular.

BACKGROUND

During operations performed to treat bone diseases of the spine, the surgeon fully or partially excises one or more vertebral bodies. The mechanical support previously given by this excised bone is therefore no longer provided. To overcome this disadvantage, rods are known to be used, generally titanium, and the spaces left empty after bone removal are filled with an inert, biocompatible material. A rod is inserted between two healthy vertebrae to provide initial support until injected cement material has hardened. An autologous single block graft, a bone from a bone bank or even a bone substitute may also be used.

Another technique consists of replacing the rod and biocompatible cement material by a rigid wired structure called a vertebral body, in which a bone graft is inserted to fill in the space left by bone removal and to provide a bony support. However to place the rigid cage in position it is necessary to draw aside adjacent vertebrae which leads to operative complications. In addition, the cage is opaque to X-rays.

SUMMARY OF THE INVENTION

One first objective of the invention is to overcome this drawback.

According to the invention, the device for repairing traumatised bone by grafting is characterized in that it comprises a tube of wide-meshed biocompatible fabric coated with a bioresorbable material wherein the graft is inserted.

By fabric is meant both knits and woven and non-woven textiles. It may or may not be bioresorbable. The tube is placed in a bone cavity to fill the empty space. But preferably, the tube is maintained in position by a plate fixed with screws onto healthy bone portions and, in the case of vertebrae, the tube is maintained in position by the vertebral plateaux of the upper and lower vertebrae.

The tube is formed of a biocompatible textile envelope, whether or not resorbable, of large mesh size. The coating material may be a compound of poly-L-Lactide, of polyglycol acid or their polymers. Poly-L-Lactide resorbs in time which allows growth of the graft through the mesh openings towards the healthy bone portions exposed by ablation. The fabric tube alone would be too flexible to ensure good contact of the implant with the healthy bone walls of the sectioned part.

Depositing bioresorbable material such as PLLA makes it possible:
  to rigidify the tube for a certain time;
  to impart a suitable anatomic shape to the tube;
  initially, to seal the tube against graft movement to avoid graft dispersion.

According to another characteristic of the invention, in the case of vertebrae, the plate also serves to hold the implant in position by at least one screw having an end embedded in the bone graft.

For vertebrae, it is known to remove all or part of the vertebral body via an anterior route which leaves the necessary room for placing the tube in position filled with grafts or compressed bone fragments. The purpose of the plate is to maintain good mechanical resistance of the structure and to maintain the tube with the filler product within a precisely delimited zone between the bones while awaiting bone consolidation.

On account of its composition, the tube is transparent to X-rays for radiographic follow-up of the development of the bone graft and for monitoring graft acceptance. The tube of fabric may be adapted to the intervertebral space by simply cutting to shape with scissors. When PLLA resorbs, the grafts can grow towards the costal walls and fuse with the latter producing the desired arthrodesis, and the tube becomes obsolete.

BRIEF DESCRIPTION OF THE DRAWINGS

Other characteristics and advantages of the invention will become apparent on reading the following description of a particular embodiment given solely as a non-limitative example with reference to the drawings which show.

DETAILED DESCRIPTION

Figure 1:
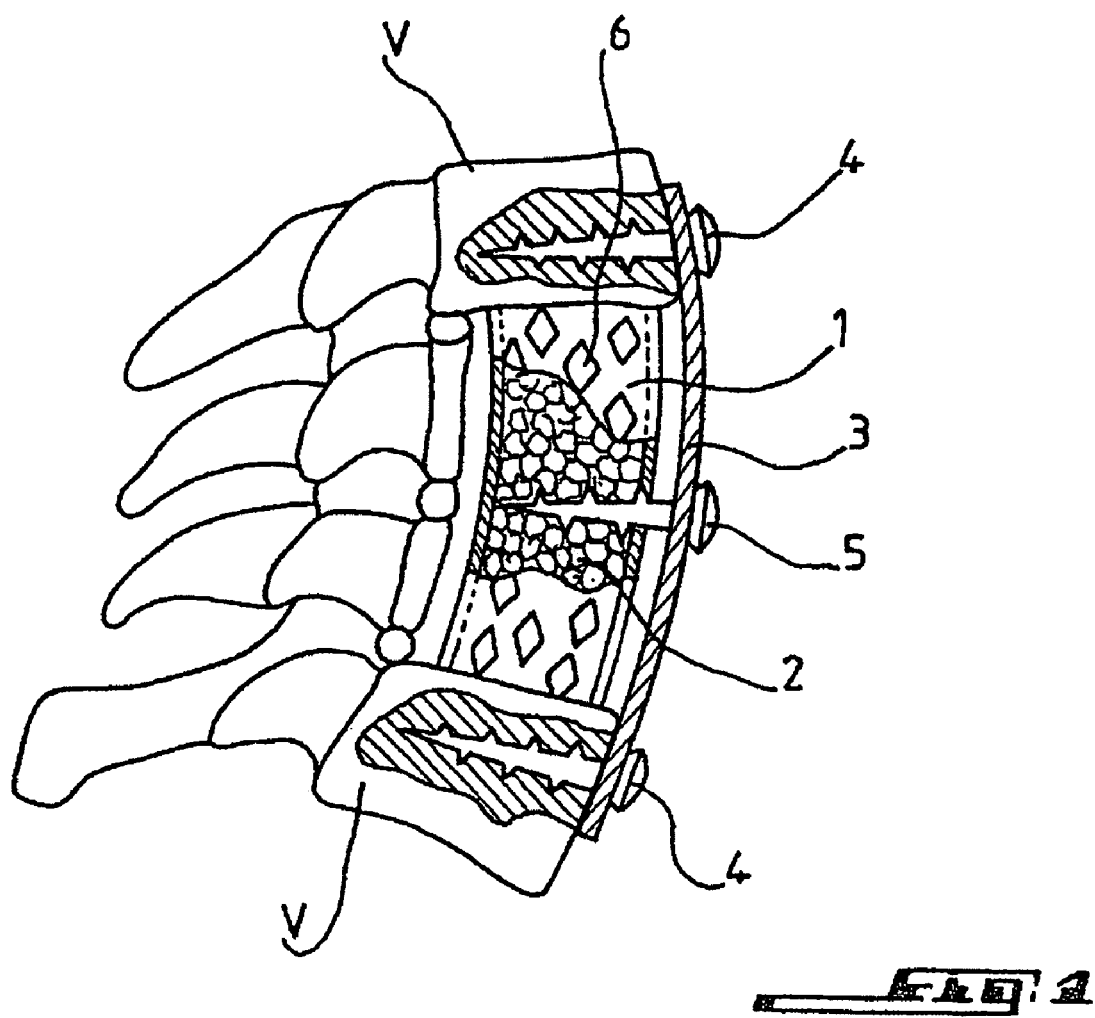
FIG. 1, a partial side, vertical section view of the implant in position within the cavity of a vertebra which has undergone corporectomy, between two healthy vertebrae.
Figure 2:
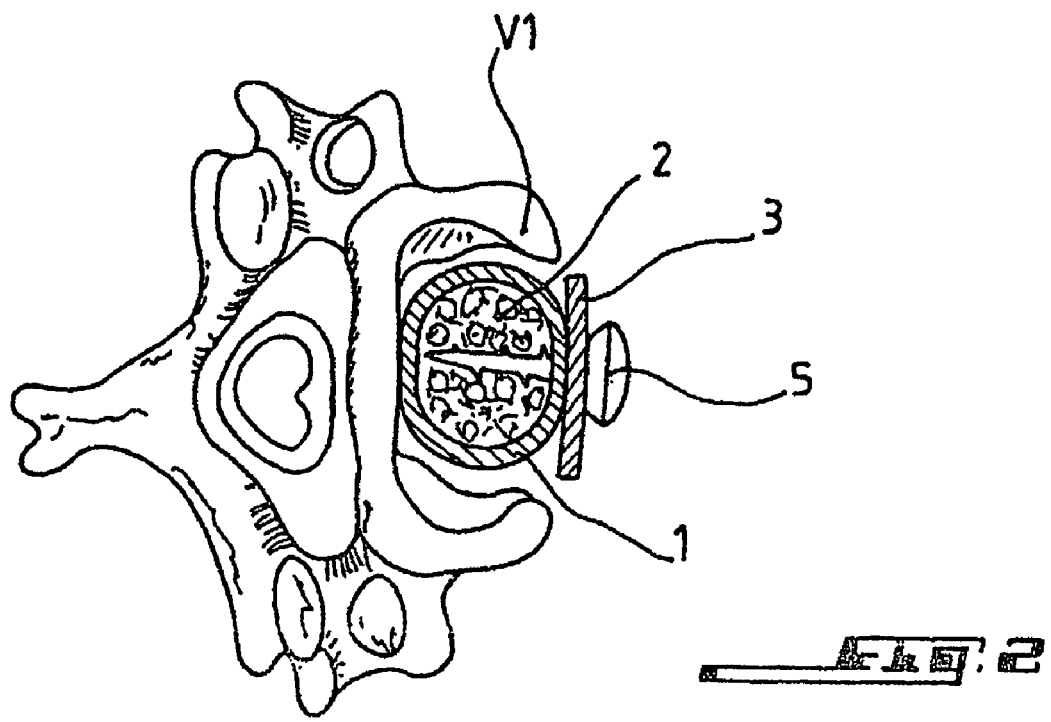
FIG. 2 is an overhead view of a horizontal section of a vertebra that has undergone partial corporectomy.

In the figures, the same reference numbers denote the same parts. In FIG. 1 it can be seen that the implant is formed by a substantially cylindrical tube 1 containing bone grafts 2, which is inserted between two healthy vertebrae V. A plate 3 is applied along the length of tube 1, the plate 3 being screwed into the vertebrae respectively above and below the vertebra which has undergone partial removal of the vertebral body. Plate 3 is held in position by securing screws 4 at its two ends, screws 4 being fixed in the two healthy vertebrae V. The implant is joined to plate 3 by at least one screw 5 which, in the example shown, is central. According to the invention, the wide meshes 6 clear after a certain time to allow growth of the grafts. Vertebral transverse and spinous processes (not referenced) can also be seen in this figure. FIG. 2 is an overhead view of the implant in position within a sectioned vertebral body V1. The medullary canal (not referenced) is schematised in this figure. In the centre of plate 3, screw 5 can be seen which passes through tube 1 and is fixed into the mass of bone grafts to secure the holding in position of tube 1.

Although the preceding description concerns vertebrae, the invention may be applied in all cases in which cavities are to be filled between two bones, in particular after excision.

It is evident that numerous variants may be made, in particular by substituting equivalent technical means, while remaining within the scope of the invention.

The invention claimed is:

1. A method for repairing bone in a bone cavity delimited by healthy bone faces, and from which traumatized bone has been excised, the method comprising:

adjusting a flexible, biocompatible mesh fabric tube to fit the bone cavity and contact the healthy bone faces, wherein the mesh is capable of allowing a bone graft within the tube to pass through the mesh;

filling the mesh tube with a bone graft;

applying a bioresorbable coating to the tube to rigidify the tube having been adjusted in shape to fit the bone cavity, wherein the coating seals the mesh against graft movement through the mesh of the tube until the bioresorbable coating has been resorbed;

inserting the tube within the bone cavity; and resorbing the coating to allow the graft to pass from the interior of the tube, through the mesh, to the healthy bone faces.

2. The method according to claim 1, further comprising holding the tube in position within the bone cavity with a plate.

3. The method according to claim 2, wherein the plate is maintained in position by screws engaging the healthy bone adjacent the bone cavity.

4. The method according to claim 3, wherein the plate is maintained in position by a screw having an end embedded in the bone graft within the tube.

5. The method according to claim 1, wherein the bone graft is selected from the group consisting of compressed bone fragments and bone substitutes.

6. The bone repair device according to claim 1, wherein the bioresorbable material contains one of poly-L-Lactide, polyglycol acid, and their copolymers.

7. The bone repair device according to claim 1, wherein the mesh textile is selected from the group consisting of knitted, woven, and non-woven fabrics.

8. The method according to claim 1, wherein the biocompatible fabric is a bioresorbable fabric.

* * * * *